US011533800B2

(12) United States Patent
Blondia

(10) Patent No.: US 11,533,800 B2
(45) Date of Patent: Dec. 20, 2022

(54) LASER SUSTAINED PLASMA AND ENDOSCOPY LIGHT SOURCE

(71) Applicant: Excelitas Technologies Singapore Pte. Ltd., Singapore (SG)

(72) Inventor: Rudi Blondia, Stockton, CA (US)

(73) Assignee: Excelitas Technologies Singapore Pte. Ltd., Singapore (SG)

( * ) Notice: Subject to any disclaimer, the term of this patent is extended or adjusted under 35 U.S.C. 154(b) by 342 days.

(21) Appl. No.: 16/704,029

(22) Filed: Dec. 5, 2019

(65) Prior Publication Data
US 2020/0187340 A1 Jun. 11, 2020

Related U.S. Application Data

(60) Provisional application No. 62/776,006, filed on Dec. 6, 2018.

(51) Int. Cl.
*H05G 2/00* (2006.01)
*H05H 1/22* (2006.01)
(Continued)

(52) U.S. Cl.
CPC ............... *H05H 1/22* (2013.01); *H01J 61/16* (2013.01); *H01J 61/30* (2013.01); *H01J 61/54* (2013.01); *H05G 2/008* (2013.01); *A61B 1/063* (2013.01)

(58) Field of Classification Search
CPC .. H05H 1/22; H01J 61/16; H01J 61/30; H01J 61/54; H01J 61/025; H01J 61/545;
(Continued)

(56) References Cited

U.S. PATENT DOCUMENTS 6,212,425 B1 4/2001 Irion et al.
6,537,211 B1 3/2003 Wang et al.
(Continued)

FOREIGN PATENT DOCUMENTS

CA 2359637 7/2000
EP 1669019 6/2006
(Continued)

OTHER PUBLICATIONS

Ye E X et al: Vis-NIR spectral flatness improvement for Laser-Driven Light Sources (LDLS}*, Microfluidics, Biomems, and Medical Microsystems XI: Feb. 3-5, 2013, San Francisco, California, United States ; [Part of Spie Photonics West]: In:Proceedings of SPIE: ISSN 0277-786X; vol. 8615; (Year: 2018).*
(Continued)

*Primary Examiner* — Donald L Raleigh
(74) *Attorney, Agent, or Firm* — Wolf, Greenfield & Sacks, P.C.

(57) ABSTRACT

An illumination source includes a laser driver unit configured to emit a plasma sustaining beam. An ingress collimator receives the plasma sustaining beam and produces a collimated ingress beam. A focusing optic receives the collimated ingress beam and produce a focused sustaining beam. A sealed lamp chamber contains an ionizable media that, once ignited, forms a high intensity light emitting plasma having a waist size smaller than 150 microns. The sealed lamp chamber further includes an ingress window configured to receive the focused sustaining beam and an egress window configured to emit the high intensity light. An ignition source is configured to ignite the ionizable media, and an exit fiber is configured to receive and convey the high intensity light. The high intensity light is white light with a black body spectrum, and the exit fiber has a diameter in the range of 200-500 micrometers.

14 Claims, 6 Drawing Sheets

(51) Int. Cl.
  *H01J 61/16* (2006.01)
  *H01J 61/30* (2006.01)
  *H01J 61/54* (2006.01)
  *A61B 1/06* (2006.01)

(58) Field of Classification Search
  CPC ........ H01J 61/548; H01J 65/04; H05G 2/008; A61B 1/063
  See application file for complete search history.

(56) References Cited

U.S. PATENT DOCUMENTS

| | | | |
|---|---|---|---|
| 6,846,311 | B2 | 1/2005 | Gatto |
| 7,037,259 | B2 | 5/2006 | Hakamata et al. |
| 7,435,982 | B2 | 10/2008 | Smith |
| 7,774,048 | B2 | 8/2010 | Nakaota et al. |
| 7,786,455 | B2 | 8/2010 | Smith |
| 7,989,786 | B2 | 8/2011 | Smith |
| 8,506,478 | B2 | 8/2013 | Mizuyoshi |
| 8,525,138 | B2 | 9/2013 | Smith et al. |
| 8,888,767 | B2 | 11/2014 | Neuberger et al. |
| 8,926,601 | B2 | 1/2015 | Neuberger et al. |
| 8,969,841 | B2 | 3/2015 | Smith |
| 9,048,000 | B2 | 6/2015 | Smith |
| 9,185,786 | B2 | 11/2015 | Smith |
| 9,456,738 | B2 | 10/2016 | Yamamoto |
| 9,609,732 | B2 | 3/2017 | Smith |
| 2009/0032740 | A1 | 2/2009 | Smith |
| 2012/0004508 | A1 | 1/2012 | McDowall et al. |
| 2015/0255949 | A1* | 9/2015 | Lee ........................ H01S 5/0071 438/26 |
| 2017/0241914 | A1 | 8/2017 | Van Heumen et al. |
| 2018/0070806 | A1 | 3/2018 | Matsuo et al. |
| 2018/0183981 | A1* | 6/2018 | Talbert ............... A61B 1/00167 |

FOREIGN PATENT DOCUMENTS

| | | | |
|---|---|---|---|
| KR | 20170007517 | | 1/2017 |
| WO | 2010065645 | | 6/2010 |
| WO | 2011100322 | | 8/2011 |
| WO | 2018/136683 | | 7/2018 |
| WO | WO-2018136683 A1 * | 7/2018 | ............ H01J 61/025 |

OTHER PUBLICATIONS

"Design and characterization of an optimized simultaneous color and near-infrared fluorescence rigid endoscopic imaging system" https://www.ncbi.nlm.nih.gov/pmc/articles/PMC3875528/ Dec. 2013.

Ye X et al: "Vis-NIR spectral flatness improvement for Laser-Driven Light Sources (LDLS)", Microfluidics, Biomems, and Medical Microsystems XI : Feb. 3-5, 2013, San Francisco, California, United States ; Ipart of SPIE Photonics Westi; In: Proceedings of SPIE; ISSN 0277-786X; vol. 8615; [Proceedings of SPIE; ISSN 0277-786X; vol. 86151, vol. 10758, Sep. 14, 2018 (Sep. 14, 2018), pp. 107580N-107580N.

International Search Report and Written Opinion for PCT/US2019/064608, dated Apr. 20, 2020.

* cited by examiner

FIG. 1
(PRIOR ART)
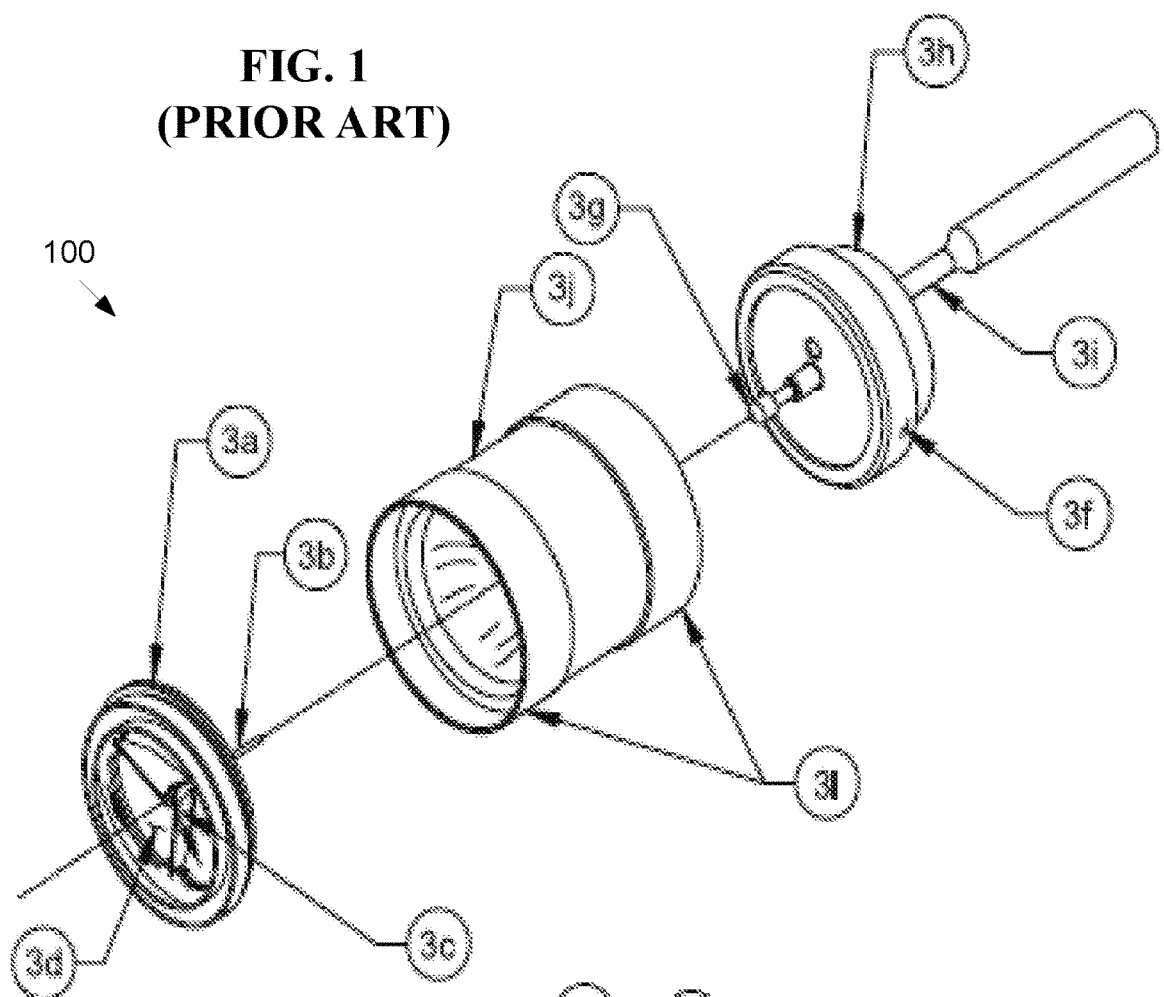
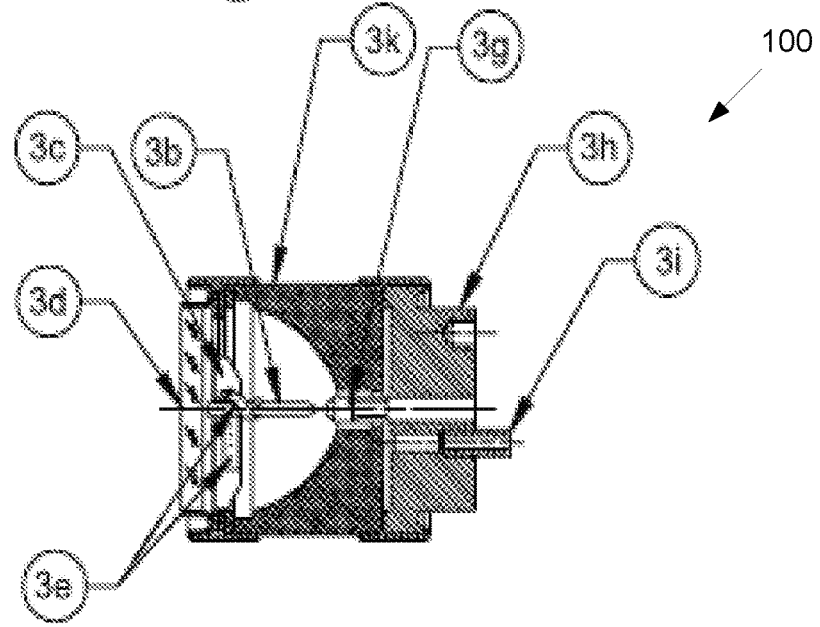
FIG. 2
(PRIOR ART)

LASER SUSTAINED PLASMA AND ENDOSCOPY LIGHT SOURCE

CROSS-REFERENCE TO RELATED APPLICATIONS

This application claims the benefit of U.S. Provisional Patent Application Ser. No. 62/776,006, filed Dec. 6, 2018, entitled "Laser Sustained Plasma and Endoscopy Light Source," which is incorporated by reference herein in its entirety.

FIELD OF THE INVENTION

The present invention relates to illumination devices, and more particularly, is related to high-intensity arc lamps.

BACKGROUND OF THE INVENTION

High intensity arc lamps are devices that emit a high intensity beam of electromagnetic radiation. The lamps generally include a gas containing chamber, for example, a glass bulb, with an anode and cathode that are used to excite the gas (ionizable medium) within the chamber. An electrical discharge is generated between the anode and cathode to provide power to the excited (e.g. ionized) gas to sustain the light emitted by the ionized gas during operation of the light source.

FIG. 1 shows a pictorial view and a cross section of a low-wattage parabolic prior art Xenon lamp 100. The lamp is generally constructed of metal and ceramic. The fill gas, Xenon, is inert and nontoxic. The lamp subassemblies may be constructed with high-temperature brazes in fixtures that constrain the assemblies to tight dimensional tolerances. FIG. 2 shows some of these lamp subassemblies and fixtures after brazing.

Referring to FIG. 1 and FIG. 2, there are three main subassemblies in the prior art lamp 100: cathode; anode; and reflector. A cathode assembly 3*a* contains a lamp cathode 3*b*, a plurality of struts holding the cathode 3*b* to a window flange 3*c*, a window 3*d*, and getters 3*e*. The lamp cathode 3*b* is a small, pencil-shaped part made, for example, from thoriated tungsten. During operation, the cathode 3*b* emits electrons that migrate across a lamp arc gap and strike an anode 3*g*. The electrons are emitted thermionically from the cathode 3*b*, so the cathode tip must maintain a high temperature and low-electron-emission to function.

The cathode struts 3*c* hold the cathode 3*b* rigidly in place and conduct current to the cathode 3*b*. The lamp window 3*d* may be ground and polished single-crystal sapphire (AlO2). Sapphire allows thermal expansion of the window 3*d* to match the flange thermal expansion of the flange 3*c* so that a hermetic seal is maintained over a wide operating temperature range. The thermal conductivity of sapphire transports heat to the flange 3*c* of the lamp and distributes the heat evenly to avoid cracking the window 3*d*. The getters 3*e* are wrapped around the cathode 3*b* and placed on the struts. The getters 3*e* absorb contaminant gases that evolve in the lamp during operation and extend lamp life by preventing the contaminants from poisoning the cathode 3*b* and transporting unwanted materials onto a reflector 3*k* and window 3*d*. The anode assembly 3*f* is composed of the anode 3*g*, a base 3*h*, and tabulation 3*i*. The anode 3*g* is generally constructed from pure tungsten and is much blunter in shape than the cathode 3*b*. This shape is mostly the result of the discharge physics that causes the arc to spread at its positive electrical attachment point. The arc is typically somewhat conical in shape, with the point of the cone touching the cathode 3*b* and the base of the cone resting on the anode 3*g*. The anode 3*g* is larger than the cathode 3*b*, to conduct more heat. About 80% of the conducted waste heat in the lamp is conducted out through the anode 3*g*, and 20% is conducted through the cathode 3*b*. The anode is generally configured to have a lower thermal resistance path to the lamp heat sinks, so the lamp base 3*h* is relatively massive. The base 3*h* is constructed of iron or other thermally conductive material to conduct heat loads from the lamp anode 3*g*. The tabulation 3*i* is the port for evacuating the lamp 100 and filling it with Xenon gas. After filling, the tabulation 3*i* is sealed, for example, pinched or cold-welded with a hydraulic tool, so the lamp 100 is simultaneously sealed and cut off from a filling and processing station. The reflector assembly 3*j* includes the reflector 3*k* and two sleeves 3*l*. The reflector 3*k* may be a nearly pure polycrystalline alumina body that is glazed with a high temperature material to give the reflector a specular surface. The reflector 3*k* is then sealed to its sleeves 3*l* and a reflective coating is applied to the glazed inner surface.

FIG. 3A shows a first perspective of a prior art cylindrical lamp 300. Two arms 345, 346 protrude outward from the sealed chamber 320. The arms 345, 346 house a pair of electrodes 390, 391, which protrude inward into the sealed chamber 320, and provide an electric field for ignition of the ionizable medium within the chamber 320. Electrical connections for the electrodes 390, 391 are provided at the ends of the arms 345, 346.

The chamber 320 has an ingress window 326 where laser light from a laser source (not shown) may enter the chamber 320. Similarly the chamber 320 has an egress window 328 where high intensity light from energized plasma may exit the chamber 320. Light from the laser is focused on the excited gas (plasma) to provide sustaining energy. The ionized media may be added to or removed from the chamber with a controlled high pressure valve 398.

FIG. 3B shows a second perspective of the cylindrical lamp 300, by rotating the view of FIG. 3A ninety degrees vertically. A controlled high pressure valve 398 is located substantially opposite the viewing window 310. FIG. 3C shows a second perspective of the cylindrical lamp 300, by rotating the view of FIG. 3B ninety degrees horizontally. In general, the interior profile of the chamber 320 matches the exterior profile of the chamber 320.

An endoscope is an illuminated optical, typically slender and tubular instrument (a type of borescope) used to look deep into the body and used in procedures called an endoscopy. It is used to examine the internal organs like the throat or esophagus. Specialized instruments are named after their target organ. Examples include the cystoscope (bladder), nephroscope (kidney), bronchoscope (bronchus), arthroscope (joints) and colonoscope (colon), and laparoscope (abdomen or pelvis). They can be used to examine visually and diagnose, or assist in surgery such as an arthroscopy. Endoscope light generating sources are typically located remotely from a light emitting aperture near the illumination target. Light is conveyed from the light source to the emitting aperture via a light guide, such as an optical fiber.

Minimally invasive endoscopic and robotic surgeries are driven by fiber optic light sources. The fibers are typically in the range of 3.0 to 4.8 mm in diameter. However, present light sources may experience a loss of radiance that may be problematic for example, in the fields of endoscopic and robotic surgery practice. Furthermore, the diameter of the fibers guiding the light is more and more prohibitive in an environment where there is a need for imaging channels and in some cases tool actuation channels in the same fiber bundle. The present trend is to seek more information out of the available space which is driving the diameter of the fibers down. For example, smaller fiber bundles may enable procedures that are currently not possible with current methods and devices. Existing light sources don't have sufficient etendue to couple significant levels of light in a fiber having a diameter smaller than 3 mm. This results in insufficient light for cameras to render a sufficiently noise free image. Therefore, there is a need to address one or more of the above mentioned shortcomings.

SUMMARY OF THE INVENTION

Embodiments of the present invention provide a laser sustained plasma and endoscopy light source. Briefly described, the present invention is directed to applications where high brightness or irradiance is delivered through small diameter light guides or fibers less than 1 mm so more space is available for imaging fibers and/or laser delivery fibers.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principles of the invention.

FIG. 1 is a schematic diagram of a prior art high intensity lamp in exploded view.

FIG. 2 is a schematic diagram of the prior art high intensity lamp of FIG. 1 in cross-section view.

DETAILED DESCRIPTION

Figure 3:
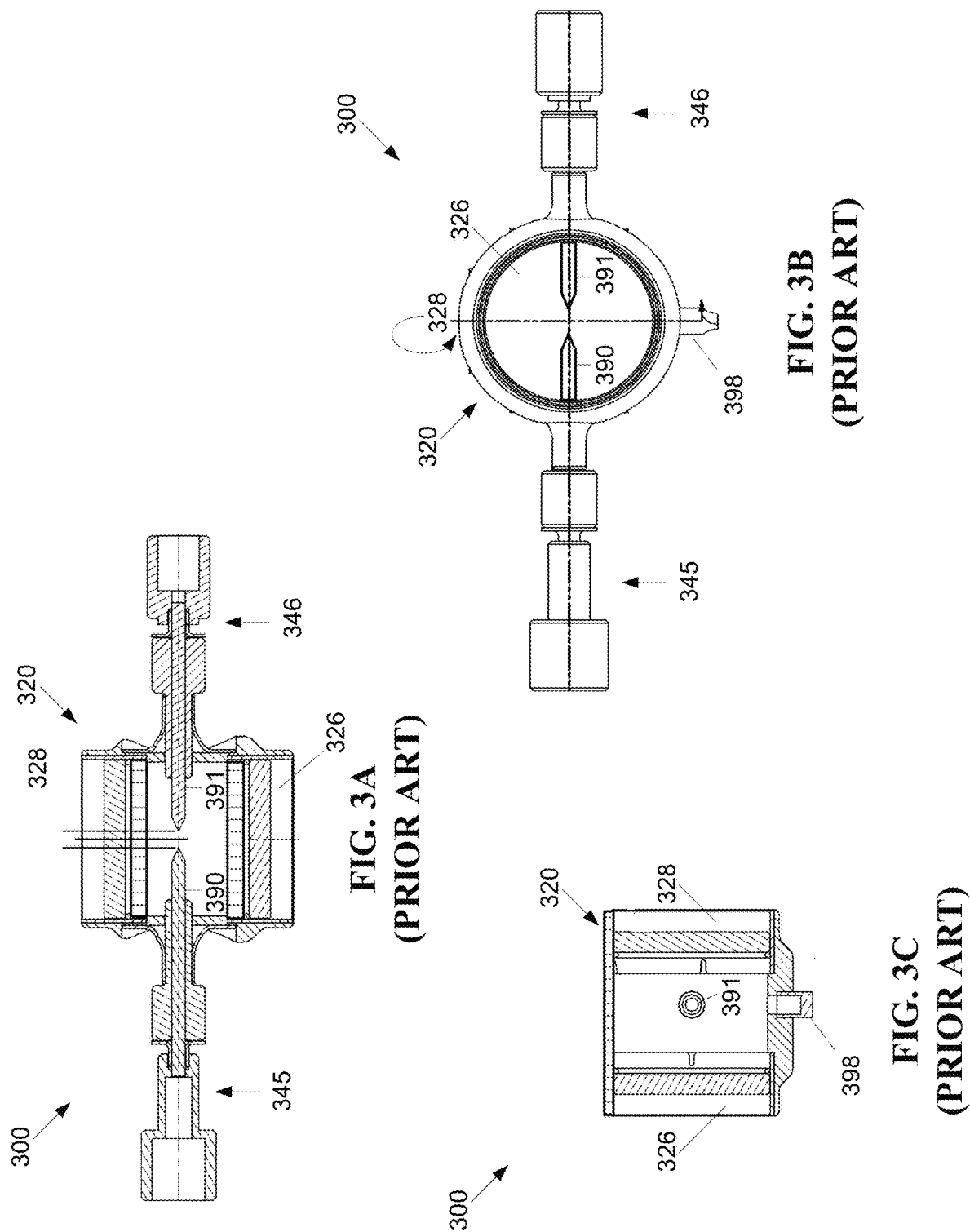
FIG. 3A is a schematic diagram of a prior art cylindrical laser driven sealed beam lamp.
FIG. 3B is a schematic diagram of the cylindrical laser driven sealed beam lamp of FIG. 3A from a second view.
FIG. 3C is a schematic diagram of the cylindrical laser driven sealed beam lamp of FIG. 3A from a third view.

The following definitions are useful for interpreting terms applied to features of the embodiments disclosed herein, and are meant only to define elements within the disclosure.

As used within this disclosure, "black body" refers to an object capable of absorbing all the electromagnetic radiation falling on it. A black body maintained at a constant temperature is a full radiator at that temperature because the radiation reaching and leaving it must be in equilibrium. A black body spectrum refers to the spectrum of electromagnetic waves a black body is able to emit.

As used within this disclosure, collimated light is light whose rays are substantially parallel, and therefore will spread minimally as it propagates.

As used within this disclosure, "substantially" means "very nearly," or within normal manufacturing tolerances. For example, a substantially flat window, while intended to be flat by design, may vary from being entirely flat based on variances due to manufacturing.

Reference will now be made in detail to embodiments of the present invention, examples of which are illustrated in the accompanying drawings. Wherever possible, the same reference numbers are used in the drawings and the description to refer to the same or like parts.

As mentioned in the Background section, minimally invasive and robotic surgeries typically use fiber optic light sources in the 3.0 to 4.8 mm diameter range. The following exemplary embodiments of the present invention describe an endoscopic light source configured to provide white light with a black body spectrum into a 200-500 micrometer fiber diameter.

Figure 4:
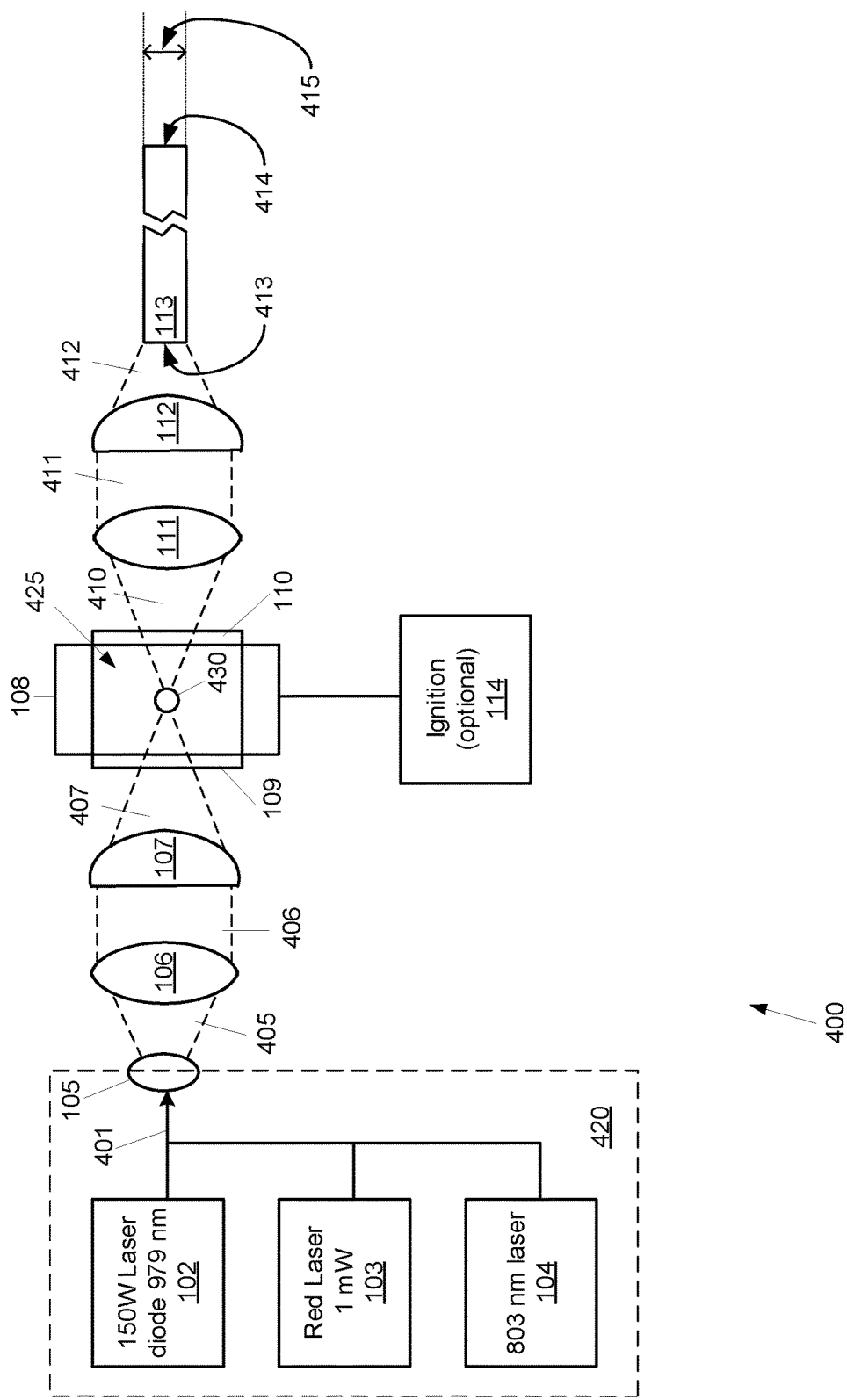
FIG. 4 is a schematic diagram of an exemplary first embodiment of lamp having a cylindrical plasma lamp chamber.

Under a first embodiment of an endoscopic light source 400 as shown by FIG. 4, a combination laser source 420 may include a plurality of laser driver units 102-104. Each laser driver unit 102-104 may emit a different wavelength/waveband and/or intensity of light. The light from the laser driver units 102-104 is combined in a light conduit 401, for example an optical fiber and emitted via an optical expander 105. Egress optics for the combination laser source 420 may be configured differently for alternative embodiments. Similarly, in alternative embodiments the combination laser source 420 may include more than three driver units or less than three driver units.

Figure 7:
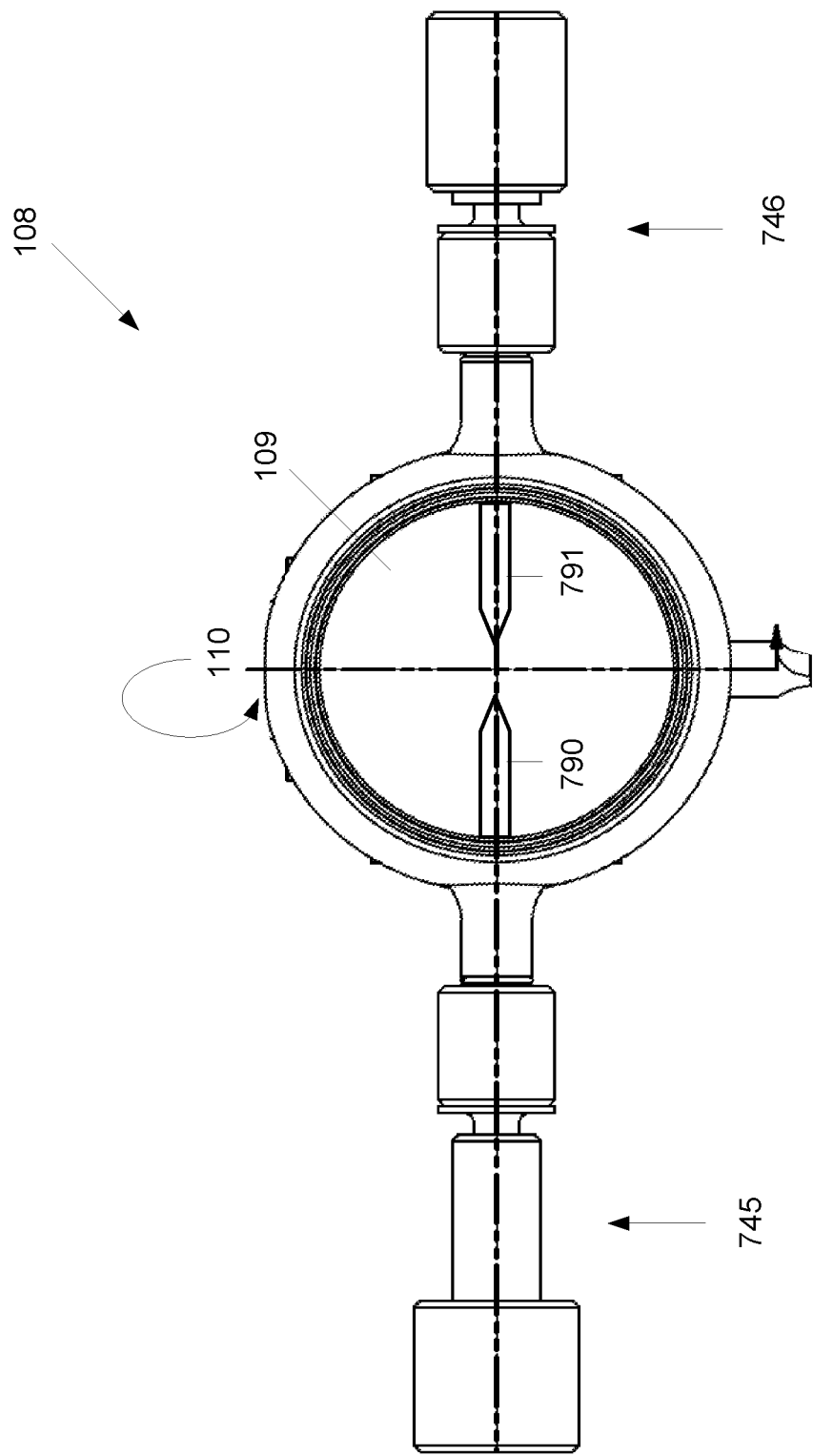
FIG. 7 is a schematic diagram detail of lamp electrodes for the first embodiment of FIG. 4.

A first laser driver unit 102 provides a portion of the beam 405. The beam 405 is collimated via an ingress collimator 106 and focused into a plasma sustaining beam 407, for example, via focusing optics 107. The plasma sustaining beam 407 enters a sealed cylindrical chamber of a lamp 108 via an ingress window 109. For example, the lamp 108 may be a cylindrical lamp. The sealed chamber of the lamp 108 contains an ionizable media 425, for example, Xenon, Krypton or a mix of Xenon and Krypton. The ionizable media 425, once ignited, forms a plasma 430 that emits a high intensity light 410. The plasma 430 is sustained by the energy from the first laser driver unit 102 via the plasma sustaining beam 407. The plasma 430 may be ignited (ionized) by an electronic ignition module 114, for example, electrodes 790, 791 (FIG. 7). The electronic ignition module 114 may provide electrical power to the electrodes 790, 791 via electrical connections in arms 745, 746 (FIG. 7) of the lamp 108. Alternatively, the electronic ignition module 114 may be omitted, and the plasma may be ignited without electrodes, for example via auto-ignition by the first laser driver unit 102.

The high intensity egress light 410 exits the chamber of the lamp 108 via an egress window 110 and is optically coupled to an exit fiber 113. For example, the high intensity egress light 410 may be substantially white in color and may be collimated into a collimated beam 411 via egress collimating optics 111, and then focused into an ingress surface 413 of the exit fiber 113 via egress focusing optics 112. For example, the collimating optics 111 may be as simple as a single positive lens, a multi lens beam expander based on positive and negative lens assembly or a parabolic mirror or combination of parabolic mirror and a combination of positive and negative lenses. The light is emitted at an egress surface 414, for example, the egress surface located at a far end of an endoscope near an illumination target. The exit fiber 113 has a fiber diameter 415 in the range of, for example, 200-500 micrometers.

The first laser driver unit 102, for example, a low power (150 Watt) 979 nm first laser driver unit 102, may generate a plasma in a Xenon, Krypton or mixed noble gas under pressures within the lamp 108 ranging from 10 bar to 50 bar with a plasma waist size of 150 microns or less that may be efficiently coupled into the diameter of the exit fiber 113, which is not possible with the standard endoscope light sources, for example a xenon short arc solution or non-laser solid state light sources.

A second laser driver unit 104 having a wavelength different from the first laser driver unit 102. For example the second laser driver unit 104 may produce an 803 nm (or other wavelength) 10-100 mW beam that may be mixed with the plasma sustaining beam produced by first laser driver unit 102 for fluorescence based diagnostics. The light from the second laser driver unit 104 is preferably mixed with visible light at the output of the lamp 108 to excite dyes for fluorescence techniques. Alternatively, the fluorescence exciting beam produced by the second laser driver unit 104 may be mixed with the high intensity light at the output of the lamp 108. For example, the beams may be mixed using a dichroic coated mirror under 45 degrees that reflects one wavelength and passes the other wavelength, where the two beams to be mixed are orthogonal while the mixing mirror is under 45 degrees. Alternatively a mix cube may be used with the same functionality. The diagonal of the cube is the mixing surface while the facets where the beams enter (orthogonally) may be coated with specific coatings to shape the properties of said beams.

The first laser driver unit 102, for example a 150 W laser diode stack is coupled, for example through beam correction optics (not shown) into a light conduit 401. Beam correction optics or shaping optics as described and needed here are used to shape the elevated diode stack light output having a different divergence in the horizontal and vertical plane into a more symmetrical beam pattern with mostly equal divergence in all directions. The light conduit 401 may be for example a 200 micrometer laser fiber keeping, for example, 95% of the power in a numerical aperture (NA) of 0.15 but other NA ranges may be practical, for example, 90% of power in a 0.2 NA or even 80% of power in a 0.3 NA. The latter two examples will exhibit lower system output but that may still be sufficient for some applications.

Since the first laser driver unit 102 produces a beam that is not visible to the human eye, a third laser driver unit 103 producing visible light, for example, a low power red laser under 5 mW may be mixed with the output of the first laser driver unit 102 and/or the second laser driver unit 104 so the optical alignment of all optical components 105, 106, 107, 111, 112 and the lamp 108 can be performed using visible light instead of using other means, for example, IR convertors to visualize the location of the 979 nm wavelength beam.

The output of the light conduit 401 may be terminated into a fiber connector (not shown) allowing for a modular approach to change out the laser drive unit(s) 102, 103, 104. The fiber connector is coupled to beam conditioning optics, for example, the optical expander 105, the ingress collimator 106, for example a collimating lens, and the ingress focusing optics 107, for example a focusing lens. The optical expander 105 shapes the beam waist of the laser in the focusing point. The NA of the ingress focusing optics 107 is preferably in the 0.4-0.6 range.

The focused output of this laser drive system including the plasma sustaining beam 407 is delivered into the lamp 108, 208 via the ingress window 109. Under the first embodiment, the lamp may be configured as a cylindrical sealed cavity lamp 108, as shown in FIG. 4 with a sapphire ingress window 109 for laser entry and a sapphire egress window 110 for high intensity visible egress light. The cylindrical sealed cavity lamp 108 generates an expanding beam 410 with a NA of 0.4-0.6. Egress collimating optics 111 receives and collimates the expanding beam 410 to produce a collimated high intensity beam 411, and an egress focusing optic 112 at the output of the lamp 108 focuses the collimated light 411 into a focused output light 412 which is introduced into the exit fiber 113.

Figure 5:
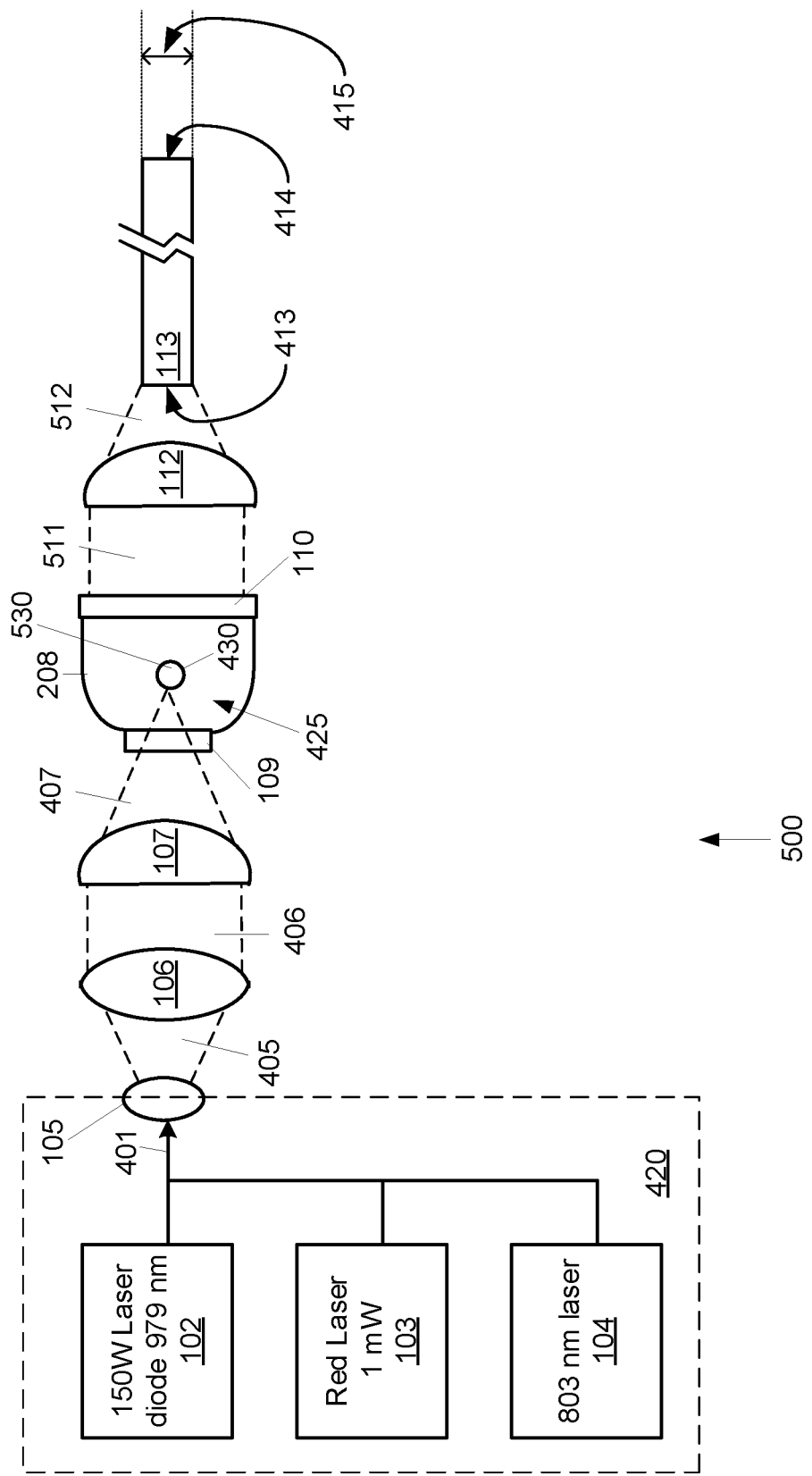
FIG. 5 is a schematic diagram of an exemplary second embodiment of lamp having a parabolic plasma lamp chamber.

A second exemplary embodiment of an endoscopic light source 500 is shown in FIG. 5. The combination laser source 420, the lamp ingress optics 106, 107, the egress focusing optic 112 and the exit fiber 113 are substantially as described in the first embodiment shown by FIG. 4.

Under the second exemplary embodiment 500, the lamp may be configured as a parabolic reflector cavity design lamp 208 with a sapphire ingress window 109 for laser entry and a sapphire egress window 110 for high intensity visible egress light. The lamp ingress optics 106, 107 focus the plasma sustaining beam 407 to a lamp focal region 530 of the parabolic reflector cavity design lamp 208, so the plasma 430 energized by the plasma sustaining beam 407 is located at the lamp focal region 530. The parabolic reflector cavity design lamp 208 reflects the high intensity light generated by the plasma 430 to produce a collimated beam 511 with a beam size limited by a diameter the egress window 110 and a configurable divergence. It should be noted that since the divergence of a parabolic reflector is determined by the diameter (or aperture) of the parabolic mirror (assuming the parabolic mirror is fully filled by the expanded light) divided by the light source (plasma) point size using, for example, a point size on the order of 150 micron, the divergence is about eight times smaller than a typical xenon lamp for endoscopy, thereby coupling more light into the exit fiber 113 than previous techniques. The egress focusing optic 112 at the output of the lamp 208 focuses the collimated beam 511 into a focused output light 512 which is introduced into the exit fiber 113.

Figure 6:
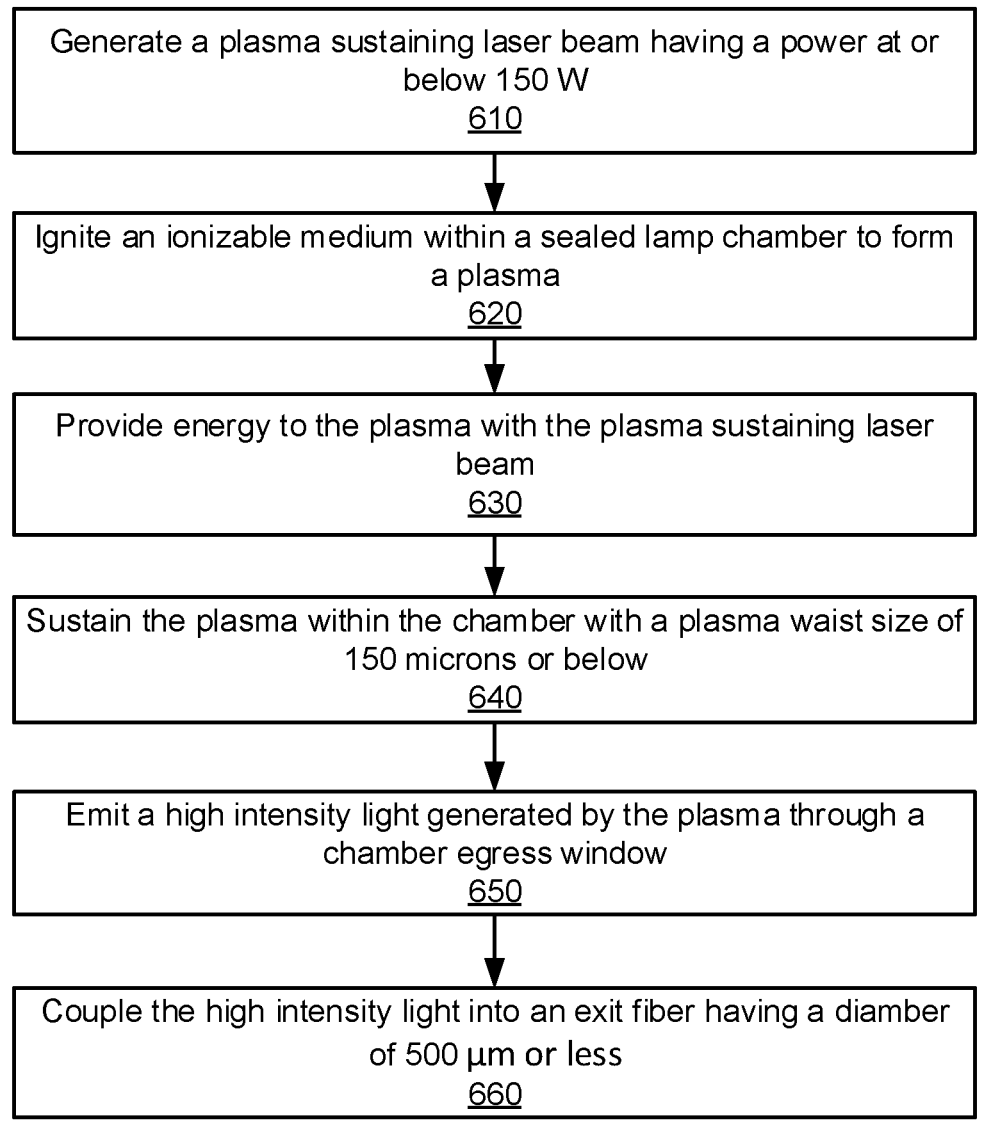
FIG. 6 is a flowchart of an exemplary embodiment of a method for producing high intensity light coupled to a small diameter light guide.

FIG. 6 is a flowchart of an exemplary embodiment of a method for producing high intensity light coupled to a small diameter light guide. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention. The method is described with reference to FIG. 4 and FIG. 6.

A plasma sustaining beam 407 having a power at or below 150 W is generated, for example, by a first laser driver unit 102 as shown by block 610. One or more other light sources may be mixed into the plasma sustaining laser beam, for example, an output of a second laser driver unit 104 producing a wavelength different from the first laser driver unit 102, for example, an 803 nm 10-30 mW laser±15 nm, and/or an output of a third laser driver unit 103 producing visible light, for example, a low power red laser. The second laser driver unit 104 preferably produces 5-10 mW of equivalent power.

An ionizable medium 425 is ignited within a sealed chamber of a lamp 108 to form a plasma 430, as shown by block 620. For example, the ionizable medium 425 may be Xenon, Krypton, or a mixture of Xenon and Krypton, among others. The ionizable medium 425 may be ignited, for example, with a pair of electrodes 790, 791 (FIG. 7) extending into the chamber of the lamp 108, by the first laser driver unit 102, and/or by non-electrode ignition agents (not shown). The plasma sustaining beam 407 is introduced into the sealed chamber of the lamp 108 via an ingress window 109, and the plasma sustaining beam 407 provides energy to sustain the plasma 430 as shown by block 630.

The plasma 430 is sustained within the chamber of the lamp 108 with a plasma waist size of 150 microns or below as shown by block 640. For example, the waist size may be controlled via the power level of the first laser driver unit 102, and/or by the lamp ingress optics 105, 106, 107. The plasma 430 emits a high intensity light 410, for example, a visible light exhibiting a black box spectra. The chamber of the lamp 108 emits the high intensity light 410 generated by the plasma 430 through a chamber egress window 110 as shown by block 650. The high intensity light 410 may be collimated into a collimated beam 411 via egress collimating optics 111, and then focused to form a focused output light 412. The focused output light 412 is coupled into an exit fiber 113 having a diameter of 500 μm or less as shown by block 660, for example, 200-500 micrometers.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An illumination source, comprising:
    an ingress laser source comprising a first laser driver unit (102) configured to emit a plasma sustaining beam;
    an ingress collimator configured to receive the plasma sustaining beam and produce a collimated ingress beam;
    an ingress focusing optic configured to receive the collimated ingress beam and produce a focused sustaining beam;
    a sealed lamp chamber containing an ionizable media that, once ignited, forms a high intensity light emitting plasma comprising a waist size smaller than 150 microns, the sealed lamp chamber further comprising:
        an ingress window configured to receive the focused sustaining beam; and
        an egress window configured to emit a high intensity light produced by the high intensity light emitting plasma;
    an ignition source configured to ignite the ionizable media; and
    an exit fiber configured to receive and convey the high intensity light,
    wherein the high intensity light comprises white light with a black body spectrum and the exit fiber has a diameter in the range of 200-500 micrometers, and the first laser driver unit further comprises a 150 W laser diode stack coupled through beam correction optics into a 200 micrometer laser fiber in a numerical aperture (NA) range of 0.15-0.3.

2. The illumination source of claim 1, wherein the ignition source further comprises a pair of electrodes.

3. The illumination source of claim 1, wherein the ignition source further comprises the first laser driver unit.

4. The illumination source of claim 1, wherein the ionizable media comprises Xenon and/or Krypton.

5. The illumination source of claim 1, wherein the plasma sustaining beam is on the order of 150 W.

6. The illumination source of claim 1, wherein the ingress laser source further comprises a second laser driver unit configured to produce a second wavelength in the range of 10-30 mW mixed with the plasma sustaining beam.

7. The illumination source of claim 6, wherein the ingress laser source further comprises a third laser driver unit configured to produce a visible beam that is mixed with the plasma sustaining beam and the second wavelength.

8. The illumination source of claim 1 wherein the sealed lamp chamber is configured as one of the group consisting of a sealed cylindrical cavity and a parabolic reflector cavity.

9. The illumination source of claim 6, wherein the ingress laser source further comprises a third laser driver unit configured to produce a visible beam that is mixed with the plasma sustaining beam and the second wavelength.

10. The illumination source of claim 9, wherein the third laser driver unit comprises a red laser with a power level of less than 5 mW.

11. The illumination source of claim 9, wherein the ingress laser source further comprises an output fiber assembly configured to receive and mix light from the first laser driver unit, the second laser driver unit, and the third laser driver unit, and the output fiber assembly is terminated into a connector coupled to an optical expander.

12. The illumination source of claim 11, wherein the optical expander is configured to shape a beam waist of received light at a focusing point, and a numerical aperture (NA) of the ingress focusing optic is in a range of 0.4-0.6.

13. A method for producing high intensity light coupled to a small diameter light guide, comprising the steps of:
    igniting an ionizable medium within a sealed lamp chamber to form a plasma;
    generating a plasma sustaining laser beam having a power at or below 150 W;
    providing energy to the plasma with the plasma sustaining laser beam;
    sustaining the plasma within the sealed lamp chamber with a plasma waist size of 150 microns or below;
    emitting a high intensity light generated by the plasma through a chamber egress window; and
    coupling the high intensity light into an exit fiber having a diameter of 500 μm or less,
    wherein a first laser driver unit configured to generated the plasma sustaining laser beam comprises a 150 W laser diode stack coupled through beam correction optics into a 200 micrometer laser fiber in a numerical aperture (NA) range of 0.15-0.3.

14. The method of claim 13, further comprising the step of mixing the plasma sustaining laser beam with a second laser beam in the range of 10-30 mW.

* * * * *

UNITED STATES PATENT AND TRADEMARK OFFICE
CERTIFICATE OF CORRECTION

PATENT NO. : 11,533,800 B2
APPLICATION NO. : 16/704029
DATED : December 20, 2022
INVENTOR(S) : Rudi Blondia It is certified that error appears in the above-identified patent and that said Letters Patent is hereby corrected as shown below:

In the Claims

At Column 7, Claim 1, Lines 43-44, "a first laser driver unit (102) configured to emit" is hereby replaced with -- a first laser driver unit configured to emit --.

Signed and Sealed this
Fourteenth Day of February, 2023

Katherine Kelly Vidal
*Director of the United States Patent and Trademark Office*